(12) United States Patent
Sedel

(10) Patent No.: US 9,789,092 B2
(45) Date of Patent: Oct. 17, 2017

(54) BIOTIN FOR USE IN TREATING X-LINKED ADRENOLEUKODYSTROPHY

(71) Applicant: Assistance Publique—Hopitaux de Paris, Paris (FR)

(72) Inventor: Frédéric Sedel, Paris (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 14/787,724

(22) PCT Filed: Jan. 14, 2014

(86) PCT No.: PCT/EP2014/050632
§ 371 (c)(1),
(2) Date: Oct. 28, 2015

(87) PCT Pub. No.: WO2014/177286
PCT Pub. Date: Nov. 6, 2014

(65) Prior Publication Data
US 2016/0074369 A1     Mar. 17, 2016

(30) Foreign Application Priority Data

Apr. 29, 2013 (WO) .................. PCT/EP2013/058936

(51) Int. Cl.
*A61K 38/43*         (2006.01)
*A61K 31/4188*     (2006.01)
*A61K 31/231*      (2006.01)
*A61K 45/06*        (2006.01)

(52) U.S. Cl.
CPC ........ *A61K 31/4188* (2013.01); *A61K 31/231* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,789,401 A | 8/1998 | McCarty | |
| 5,929,066 A | 7/1999 | McCarty | |
| 6,660,251 B1 * | 12/2003 | Bunger | A61K 8/42 424/401 |
| 6,664,039 B1 * | 12/2003 | Benzer | C12N 9/1029 435/183 |
| 8,609,165 B1 | 12/2013 | Andrews et al. | |
| 8,835,487 B2 | 9/2014 | Sedel | |
| 9,351,961 B2 | 5/2016 | Sedel | |
| 2005/0256178 A1 * | 11/2005 | Eggersdorfer | A21D 2/36 514/393 |
| 2006/0068016 A1 | 3/2006 | Kidokoro et al. | |
| 2007/0231405 A1 | 10/2007 | Gorban | |
| 2013/0084334 A1 | 4/2013 | Sedel et al. | |

FOREIGN PATENT DOCUMENTS

| | | |
|---|---|---|
| BG | 66011 B1 | 10/2010 |
| JP | 9095448 A | 4/1997 |
| WO | 2004/017766 A1 | 3/2004 |
| WO | 2011/124571 A1 | 10/2011 |

OTHER PUBLICATIONS

Engelen et al., Orphanet Journal of Rare Diseases, 7(51):1-14 (2012).*
Moser et al., J. Inherit. Metab. Dis., 23: 273-277 (2000).*
Health Monthly, <https://www.healthmonthly.co.uk/swanson_ultra_time_release_biotin_10mg>, Apr. 12, 2014 (Accessed Oct. 3, 2016).*
TL-HEM 150, Technical Specification (2011).*
Bhagavan et al., J. Neurochem., 17:289-290 (1970).*
Goncalves et al., JACOS, 68(7):474-480 (1991).*
Baumgartner et al., Am. J. Hum. Genet., 75:790-800 (2004).*
Markovic-Plese et al., Future Neurol., 3(2):1-21 (2008).*
Pai et al., Mol. Gen. Metab., 69:312-322 (2000).*
Aubourg et al., NEJM, 329(11):745-752 (1993).*
Berger et al., Brain Pathol., 20(4):845-856 (2010.*
Kopinski et al., Brit. J. Nutr., 62:761-766 (1989).*
Shen et al., (Proc. Soc. Exp. Biol. Medic., 146:21-24 (1974).*
Zempleni et al., Am. J. Clin. Nutr., 69:504-508 (1999).*
Moser et al., J. Mol. Neurosci., 33:105-113 (2007).*
Johannes Berger et al., "Current and Future Pharmacological Treatment Strategies in X-Linked Adrenoleukodystrophy," Brain Pathology, vol. 20, No. 4, pp. 845-856, XP055104800, ISSN 1015-6305 (Jan. 8, 2010).
Alexander Semmler et al., "Therapy of X-linked adrenoleukodystrophy," Expert Review of Neurotherapeutics, vol. 8, No. 9, pp. 1367-1379, XP009150422, ISSN 1473-7175 (Jan. 1, 2008).
Brück, The pathology of multiple sclerosis is the result of focal inflammatory demyelination with axonal damage, abstract, J Neurol. Nov. 2005;252 Suppl 5:v3-9.
Politte et al., Neuropsychiatric Manifestations of Multiple Sclerosis, 10 Prim Care Companion J Clin Psychiatry 318, 318-324 (2008).
Chakraborty, G. and Ledeen, R. "Fatty acid synthesizing enzymes intrinsic to myelin", Molecular Brain Research, vol. 112, pp. 46-52, 2003.
Chaudhuri, A. et al., "Multiple Sclerosis is Not an Autoimmune Disease", Arch Neurol, vol. 61, pp. 1610-1612, 2004.
Tong, L., "Structure and funciton of biotin-dependent carboxylases", Cell. Mol. Life Sci., vol. 70, pp. 863-891, 2013 (published online Aug. 7, 2012).
Stys, P.K. et al., "Will the real multiple sclerosis please stand up?", Nature Reviews/Neuroscience, vol. 13, pp. 507-514 and Erratum (1 page), Jul. 2012.
Luessi, F. et al., "Neurodegerneration in multiple sclerosis: novel treatment strategies", Expert Rev. Neurother., vol. 12, No. 9, pp. 1061-1077, 2012.
Anagnostouli, M. et al., "Biotin in CSF and Serum in Patients with Multiple Sclerosis," Journal of the Neurological Sciences, vol. 150, Suppl. 1, p. S47 Abstract 1-31-03, Sep. 1997.
Baumgartner, M., "3-Methylcrotonyl-CoA carboxylase deficiency," Orphanet Encyclopedia, (2005), p. 1-7.

(Continued)

*Primary Examiner* — Thomas J Visone
(74) *Attorney, Agent, or Firm* — Rothwell, Figg, Ernst & Manbeck, P.C.

(57) ABSTRACT

The invention relates to the use of biotin for treating X-linked adrenoleukodistrophy, in particular adrenomyeloneuropathy.

13 Claims, No Drawings

(56) References Cited

OTHER PUBLICATIONS

Breedon, C., "Aunt Cathy's Guide to Nutrition: Nutriton Issues in Multiple Sclerosis", MeritCare Health System, (2009), p. 1-29.
Darin et al., "3-Methylcrotonyl-CoA Carboxylase Deficiency and Severe Multiple Sclerosis," Pediatric Neurology, vol. 36, No. 2, (2007), p. 132-134.
Shirazi et al., "Dietary Supplementation in Iranian Multiple Sclerossi Patients," J. Med. Sci., vol. 7, No. 3, (2007), p. 413-417.
Yang et al., "Spinal Cord Demyelination Associated with Biotinidase Deficiency in 3 Chinese Patients," Journal of Child Neurology, vol. 22, No. 2, (2007), p. 156-160.
Jane M. Rodgers, et al., "Strategies for Protecting Oligodendrocytes and Enhancing Remyelination in Multiple Sclerosis," Discovery Medicine, vol. 16, No. 86, pp. 53-63, ISSN: 1539-6509; eISSN: 1994-7930 (Aug. 2013).
PCT International Search Report and Written Opinion, issued in PCT/EP2014/05632 dated Mar. 7, 2014, 9 pages.
"Biotin," Alternative Medicine Review, vol. 12, No. 1, pp. 73-78 (Mar. 2007).
*Personal Web Technologies, LLC* v. *Apple, Inc.*, (Fed. Cir. 2017), 13 pages.
Institute of Medicine (US) Standing Committee on the Scientific Evaluation of Dietary Reference Intakes and its Panel on Folate, Other B Vitamins, and Choline, "Biotin," The National Academies Press, (1998), 17 pages.
Institute of Medicine (US) Standing Committee on the Scientific Evaluation of Dietary Reference Intakes and its Panel on Folate, Other B Vitamins, and Choline, "Dietary Reference Intake for Thiamin, Riboflavin, Niacin, Vitamin B6, Folate, Vitamin B12, Pantothenic Acid, Biotin, and Choline," The National Academies Press, (1998), 592 pages.
Melissa Cambron et al., "White-matter astrocytes, axonal energy metabolism, and axonal degeneration in multiple sclerosis," Journal of Cerebral Blood Flow & Metabolism, vol. 32, pp. 413-424 (2012).
Graham R. Campbell et al., "Mitochondrial Changes Associated with Demyelination: Consequences for Axonal Integrity," Mitochondrion, vol. 12(2), pp. 173-179 (2012).
Jeremy Chataway, "Biotin in progressive multiple sclerosis: A new lead?" Multiple Sclerosis Journal, vol. 22(13), pp. 1640-1641 (2016).
Rebecca Heidker et al., "Intersections of Pathways Involving Biotin and Iron Relative to Therapeutic Mechanisms for Progressive Multiple Sclerosis," Discovery Medicine, vol. 22(123), pp. 381-387 (2016).
Hans Lassmann et al., "The molecular basis of neurodegeneration in multiple sclerosis," FEBS Letters, vol. 585(23), pp. 3715-3723 (2011).
Daniel Ontaneda, "Clinical trials in progressive multiple sclerosis: lessons learned and future perspectives," Lancet Neurology, vol. 14(2), pp. 208-223 (Feb. 2015).
Daniel Ontaneda et al., "Progressive multiple sclerosis," Curr Opin Neurol., vol. 28(3), pp. 237-243 (Jun. 2015).
Frédéric Sedel et al., "High doses of biotin in chronic progressive multiple sclerosis: A pilot study," Multiple Sclerosis and Related Disorders, vol. 4, pp. 159-169 (2015).
Frédéric Sedel et al., "Targeting demyelination and virtual hypoxia with high-dose biotin as a treatment for progressive multiple sclerosis," Neuropharmacology, vol. 110, pp. 644-653 (2016).
Singer GM et al., "The effect of chromium picolinate and biotin supplementation on glycemic control in poorly controlled patients with type 2 diabetes mellitus: a placebo-controlled, double-blinded, randomized trial," Diabetes Technol Ther., vol. 8(6), pp. 636-643 (Dec. 2006).
Christine Stadelmann, "Multiple sclerosis as a neurodegenerative disease: pathology, mechanisms and therapeutic implications," Current Opinion in Neurology, Vo. 24, pp. 224-229 (2011).
Ayman Tourbah et al., "MD1003 (high-dose biotin) for the treatment of progressive multiple sclerosis: A randomised, double-blind, placebo-controlled study," Multiple Sclerosis Journal, vol. 22(13), pp. 1719-1731 (2016).

Catriona A. Wagner et al., Novel Insights and Therapeutics in Multiple Sclerosis [v1; ref status: indexed, http://f1000r.es/59z], F1000Research, vol. 4(F1000 Facilty Rev), 8 pages (2015).
"Vitamins Fight Multiple Sclerosis," Orthomolecular Medicine News Service, 2 pages (Oct. 4, 2006).
Albarracin, Cesar et al., "Combination of Chromium and Biotin Improves Coronary Risk Factors in Hypercholesterolemic Type 2 Diabetes Mellitus: A Placebo-Controlled, Double-Blind, Randomized Clinical Trial," Journal of Cardiometabolic Syndrome, 2007, pp. 91-97, Spring: vol. 2 No. 2.
Albarracin, Cesar et al., "Chromium picolinate and biotin combination improves glucose metabolism in treated, uncontrolled overweight to obese patients with type 2 diabetes," Diabetes/Metabolism Research and Reviews, 2008, pp. 41-51, vol. 24.
Báez-Saldaña, Armida et al., "Effects of biotin on pyruvate carboxylase, acetyl-CoA carboxylase, propinoyl-CoA carboxylase, and markers for glucose and lipid homeostasis in type 2 diabetic patients and nondiabetic subjects," The American Journal of Clinical Nutrition, 2004, pp. 238-243, vol. 79.
Dabbagh, O., et al. "The Clinical Spectrum of Biotini-Treatable Encephalopathies in Saudi Arabia", Brain & Development, vol. 16 (suppl.), (1994), pp. 72-80.
Debs, Rabab, et al., "Biotin-Responsive Basal Ganglia Disease in Ethnic Europeans with Novel SLC19A3 Mutations", Arch. Neurol., vol. 67, No. 1, (2010), pp. 126-130.
M. Anagnostouli et al., "Cerebrospinal fluid levels of biotin in various neurological disorders," Acta Neurologica Scandinavica, vol. 99, pp. 387-392, ISSN 0001-6314 (Jan. 1, 1999).
Fuhr, Joseph P. Jr. et al., "Use of Chromium Picolinate and Biotin in the Management of Type 2 Diabetes: An Economic Analysis," Disease Management, 2005, pp. 265-275, vol. 8 No. 2.
Geohas, Jeff et al., "Chromium Picolinate and Biotin Combination Reduces Atherogenic Index of Plasma in Patients with Type 2 Diabetes Mellitus: A Placebo-Controlled, Doubled-Blinded, Randomized Clinical Trial," The American Journal of Medical Sciences, 2007, pp. 145-153, vol. 333 No. 3.
Hemmati, Mitra et al., "Survey of the Effect of Biotin on Glycemic Control and Plasma Lipid Concentrations in Type 1 Diabetic Patients in Kermanshah in Iran (2008-2009)" Oman Medical Journal, 2013, pp. 195-198, vol. 28. No. 3.
Hooton et al., "methionine," Handbook of Pharmaceutical Excipients, Sixth Edition, pp. 436-437 (Feb. 27, 2009).
Klenner, F., "Response of Peripheral and Central Nerve Pathology to Mega-Doses of the Vitamin B-Complex and Other Metabolites—Part 1," Journal of Applied Nutrition, vol. 25 (18 pages), (1973).
Klenner, F., "Response of Peripheral and Central Nerve Pathology to Mega-Doses of the Vitamin B-Complex and Other Metabolites—Part 2," Journal of Applied Nutrition, vol. 25 (11 pages), (1973).
McCarty, M.F., "High-dose biotin, an inducer of glucokinase expression, may synergize with chromium picolinate to enable a definitive nutritional therapy for type II diabetes," Medical Hypotheses, 1999, pp. 401-406, vol. 52 No. 5.
McCarty, M.F., "cGMP may have trophic effects on beta cell function comparable to those of cAMP, implying a role for high-dose biotin in prevention/treatment of diabetes," Medical Hypotheses, 2006, pp. 323-328, vol. 66.
McCarty, M.F., "Exenatide and biotin in conjunction with a protein-sparing fast for normalization of beta cell function in type 2 diabetics," Medical Hypotheses, 2007, pp. 928-932, vol. 69.
Nanric, Inc., "Nanric Extra Strength Biotin 100," published online on Apr. 13, 2004, available at http://www.nanric.com/catalong/all-products/biotin-100-1-gallonbucket (3 total pages).
Ozand, Pinar T., et al., "Biotin-Responsive Basal Ganglia Disease: a Novel Entity", Brain, vol. 121, (1998), pp. 1267-1279.
Duertas, Bordallo D., et al., "Optic Neuropathy in Biotinidase Deficiency", Arch. Soc. Esp. Optalmol. vol. 79 (20040, pp. 393-396. (2004).
Rabin, B., "Inhibition of Experimentally Induced Autoimmunity in Rats by Biotin Deficiency," American Institute of Nutrition, vol. 113(11):2316-2322, (Nov. 1983).
Rahman, Shamima, et al., "Late Presentation of Biotinidase Deficiency with Acute Visual Loss and Gait Disturbance", Developmental Medicine & Child Neurology, vol. 39, (1997), pp. 830-831.

(56) References Cited

OTHER PUBLICATIONS

Ramaekers, V. Th., et al. A Biotinidase Km Variant Causing Late Onset Bilateral Optic Neuropathy, Archives of Disease in Childhood, vol. 67, (1992), pp. 115-119.

Revilla-Monsalve, Cristina et al., "Biotin supplementation reduces plasma triacylglycerol and VLDL in type 2 diabetic patients and in nondiabetic subjects with hypertriglyceridemia," Biomedicine & Pharmacotherapy, 2006, pp. 182-185, vol. 60.

Sedel, F., et al., "Leukoencephalopathies Associated with inborn Errors of Metabolism in Adults", J. Inherit. Metab. Dis., (2008), 13 pages.

Singer, Gregory M., "The Effect of Chromium Picolinate and Biotin Supplementation on Glycemic Control in Poorly Controlled Patients with Type 2 Diabetes Mellitus: A Placebo-Controlled, Double-Blinded, Randomized Trial," Diabetes Technology and Therapeutics, 2006, pp. 636-643, vol. 6.

Straussberg, R., et al., Familial Infantile Bilateral Striatal Necrosis:, Neurology, vol. 59, (2002), pp. 983-989.

Subramanian, Veedamali S., et al., "Biotin-Responsive Basal Ganglia Disease-Linked Mutations Inhibit Thiamine Transport via hTHTR2: Biotin is not a Substrate for hTHTR2", Am. J. Physiol., vol. 291, (2006), pp. C851-C859.

Sugita, Yumi et al.,, "Effect of Biotin Treatment on Hepatic Gene Expression in Streptozotocin-Induced Diabetic Rats," Biosci. Biotechnol. Biochem, 2008, pp. 1290-1298, vol. 72. No. 5.

Trevor A. Wing, "Thrush (Candida albicans)," Woman's Natural Health Practice: Candida (thrush), website available at http://www.naturalgynae.com/nav6_fact2.html, accessed on Oct. 13, 2014 and webpage originally captured on Mar. 30, 2003 (3 total pages).

U.S. Appl. No. 61/270,030, filed Jul. 2, 2009.

Vlasova, Tatyana I., et al., "Biotin Deficiency Reduces Expression of SLC19A3, a Potential Biotin Transporter, in Leukocytes from Human Blood", J. Nutr., vol. 135 No. 1, (2005), pp. 42-47.

Weber Peter, et la., "Outcome in Patients with Profound Biotinidase Deficiency: Relevance of Newborn Screening", Developmental Medicine & Child Neurology, vol. 46, (2004), pp. 481-484.

Wolf, Barry, "Clinical Issues and Frequent Questions about Biotinidase Deficiency", Molecular Genetics and Metabolism, vol. 100, (2010), pp. 6-13.

Wolf, Barry, "The Neurology of Biotinidase Deficiency", Molecular Genetics and Metabolism, vol. 104, Nos. 1-2 (2011), pp. 27-34.

XP-002599161—English language Abstract of JP-9095448, Apr. 8, 1997 (cited in International Search Report).

Zempleni, Janos, et al., "Biotin", BioFactors, vol. 35, No. 1, (2009), pp. 36-46.

Zeng, Wen-Qi, et al., "Biotin-Responsibe Basal Ganglia Disease Maps to 2q36.3 and is due to Mutrations in SLC19A3", Am. J. Hum. Genet., vol. 77, (2005), pp. 16-26.

Zhuolin Liu et al., "Multiple sclerosis is an autoimmune disease," Neurogenetic Diseases, People's Medical Publishing House, p. 478, Apr. 2002.

* cited by examiner

BIOTIN FOR USE IN TREATING X-LINKED ADRENOLEUKODYSTROPHY

This application is a National Phase of International Application Serial No. PCT/EP2014/050632, filed Jan. 14, 2014, which claims priority of International Application Serial No. PCT/EP2013/058936, filed on Apr. 29, 2013, which are incorporated herein by reference in their entireties.

The invention relates to the treatment of X-linked adrenoleukodystrophy, and in particular adrenomyeloneuropathy.

X-linked adrenoleukodystrophy (ALD) is a rare inherited peroxisomal neurodegenerative disorder due to a loss of function of a fatty acid transporter, the ALD protein, encoded by the ABCD1 gene. The incidence of X-ALD is 1/17,000 births, including hemizygotes and heterozygous women who often present with symptoms in adulthood. Prevalence is estimated at 1/20,000.

The X-ALD clinical spectrum ranges from the childhood cerebral form (CCALD) which is characterized by rapid cerebral demyelination with onset in the first decade (approx. 40% cases) that leads to death within few years, to the milder adrenomyeloneuropathy (AMN) that manifests in adulthood, affects the axons in the spinal cord and may be compatible with survival up to the eighth decade (approx. 60% of cases). X-ALD males may present with isolated Addison's disease years or decades before the onset of CCALD or AMN.

AMN, the most frequent X-ALD phenotype, is characterized by the onset of spastic paraparesia between 20 and 45 years of age, that results in progressive stiffness and weakness of the legs, sensory ataxia with gait disturbance and impaired vibration sense in the lower limbs, sphincter disturbances and impotence. The evolution of AMN in adult males and heterozygous women is quite variable; a relapsing and remitting evolution is however never seen. Within 10-15 years, motor disability becomes severe in most affected patients and requires the use of a cane or a wheelchair.

The neuropathology of AMN is characterized by loss of axons in the long tracts of the spinal cord, mainly dorsal fascicles and pyramidal tracts, and secondary and mild loss of myelin. Biochemically, mutations of the ABCD1 gene encoding for the ALD protein lead to impaired import of very long chain fatty acids (VLCFAs) in peroxisomes. Hence, VLCFAs cannot be degraded through peroxisomal β-oxidation and accumulate in body tissues and fluids. The accumulation of VLCFA generates oxidative stress (Powers et al., 2005) and mitochondrial anomalies (Fourcade et al., 2008) that contributes to the pathogenesis of AMN. It is likely that in AMN, oxidative stress and mitochondrial abnormalities in oligodendrocytes of spinal cord may impair their capacity to sustain axonal integrity resulting in axonal damage.

There are currently no satisfactory treatments for X-ALD and AMN. Treatments include genic therapy, or use of Lorenzo's oil to prevent onset of the disease, although therapeutic activity of said oil if still discussed.

Biotin (or vitamin H) is a ubiquitous water-soluble vitamin which is naturally found in many foods, such as offal, eggs and certain vegetables. In mammals, biotin acts as a cofactor for four metabolism carboxylases involved in several key steps of energy metabolism, including pyruvate carboxylase (neoglucogenesis), 3-methylcrotonyl CoA and propionyl CoA carboxylases (catabolism of certain amino acids which supply the Krebs cycle with intermediate metabolites), and acetyl CoA carboxylase (fatty acid synthesis).

Consequently, the mechanism of action of biotin can bee seen as an enhancer of brain energy (ATP) production.

The inventor has thus tested this compound, considering it as a good candidate to enhance functional recovery in X-ALD and AMN.

Patent application WO 2011/124571 describes the use of biotin at a high dose (of the order of 100 to 600 mg/day) for the treatment of visual impairments, in particular related to optic atrophy. It should be noted that the visual impairments actually described in this application are symptoms related to a particular leukoencephalopathy, i.e. an involvement of the white matter of the brain. This document neither describes nor suggests that biotin could be used for the treatment of adrenomyeloneuropathy.

In the context of the present invention, it has, in fact, been shown that biotin, in particular at a high dose, can make it possible to improve the condition of patients suffering from X-ALD, more specifically AMN.

As it will be seen in the example, improvement has been observed in a patient with adrenomyeloneuropathy, with an improved physical capacity and functional improvement of a side-effect of the disease (urinary problems).

The invention thus relates to biotin for use thereof in the treatment of X-linked adrenoleukodystrophy, and especially of adrenomyeloneuropathy.

Also subjects of the invention are compositions containing biotin for the use thereof in the treatment of X-linked adrenoleukodystrophy, and also the use of biotin for the production of a drug intended for the treatment of X-linked adrenoleukodystrophy. The teachings of the invention thus make it possible to implement treatment methods comprising the administration of biotin to patients suffering from X-linked adrenoleukodystrophy, in particular of adrenomyeloneuropathy. The invention thus also relates to a method for treating a patient suffering from X-linked adrenoleukodystrophy, comprising the step of administering biotin to said patient.

Biotin can be used alone or in combination with another compound used for treating X-linked adrenoleukodystrophy, such as Lorenzo's oil (4 parts of glyceryl trioleate and 1 part glyceryl trierucate) or Fampridine (4-Aminopyridine). The invention therefore covers a composition containing biotin and also another medicament against X-linked adrenoleukodystrophy, for simultaneous, separate or sequential (spread out over time) use in the treatment of X-linked adrenoleukodystrophy.

The invention also relates to biotin for use thereof in the treatment of X-linked adrenoleukodystrophy (X-ALD). In particular, the invention relates to biotin for use thereof in the treatment of adrenomyeloneuropathy (AMN).

The biotin is preferentially administered at a high dose, i.e. at a dose greater than 50 mg per day. Even if a maximum dose is not really envisaged, the latter should not generally exceed 500 mg, 600 mg or 700 mg per day. In that way, a dose at least equal to 1 mg/kg/day, preferably 3 mg/kg/day, preferably 5 mg/kg/day, or at least equal to 7.5 mg/kg/day, or even around 10 mg/kg/day, is administered to the patient. Between 50 and 700 mg of biotin per day are thus administered to the patients, generally between 50 and 500 mg per day, or between 50 and 600 mg per day, more preferably between 100 and 300 mg per day, generally around 300 mg per day. One can thus administered at least 50 mg par day, more preferably at least 100 mg per day, or at least 150 mg per day, or even 200 or 250 mg per day.

In one particular embodiment which is preferred (in particular for problems of ease of use by the patient), the biotin is in a form suitable for oral administration. This therefore involves a composition for oral administration, which will contain at least 20 mg, preferably at least 40 mg of biotin, or even 50 mg, 75 mg, 100 mg, 150 mg or 250 mg of biotin. This composition is preferentially for pharmaceutical use, and is therefore a medicine. It is understood that each unit dose of this composition contains at least 20 mg, preferably at least 40 mg, or even 50 mg, 100 mg, 150 mg or 250 mg of biotin, as active ingredient.

In one particular embodiment, this composition for oral administration contains biotin as sole active ingredient, and also excipients, without any other active ingredient.

An excipient should be understood to mean any compound forming part of the formulation which is intended to act as a simple support, i.e. which is not intended to have a biological activity.

This composition can be in any form known in the art. In particular, it is in the form of gel capsules, tablets (optionally film-coated), pills or lozenges. In another embodiment, it is in the form of a syrup. Said syrup contains an amount such that it contains at least 20 mg, preferably at least 40 mg, or even 50 mg, 75 mg or 100 mg of biotin per unit dose. The concentration of biotin in this syrup depends on the unit dose that it is desired to give to the patient.

Excipients which can be used by those skilled in the art are well known in the art. Talc (E553b), microcrystalline cellulose, lactose, mannose, starch (in particular corn starch), magnesium stearate (E572) and stearic acid (E570) can thus be chosen. This list is not exhaustive.

When this composition is prepared in the form of 25 gel capsules, a preferred excipient is microcrystalline cellulose.

When the composition is in the form of a film-coated tablet, said film-coating may be formed from any substance known in the art, such as hypromellose (E464), ethylcellulose, macrogol, talc (E553b) titanium dioxide (E171) or iron oxide (E172).

The active ingredient may also be colored (by any acceptable coloring, such as cochineal), thereby making it possible to verify that the biotin is well dispersed in the excipient.

A slow release (or slow sustained) form may also be envisaged given the fact that plasma half life of biotin is short (about 2 hours).

Said slow release compositions are known in the art and described in particular in WO 2011/077239. In particular, said slow release compositions may comprise a slow release matrix comprising biotin alone or with one or more active ingredient(s).

In a specific embodiment, the slow release composition comprises a matrix allowing immediate release, wherein said matrix comprises biotin alone or with one or more other active ingredient(s) and the slow release is achieved by a release modifying matrix or coating.

Thus, the slow release composition may provide immediate release and differed (slow) release of biotin.

In a specific embodiment slow release may be achieved through an osmotically driven release system.

In another embodiment, the slow release composition comprises a core comprising biotin, optionally one or more active ingredient(s), and optionally pharmaceutical excipient(s) and one or more outer layers, wherein the outer layers comprises one or more slow release agent(s).

In another aspect, the biotin may be in the form which allows administration by injection: this then involves an injectable composition containing at least 20 mg, preferably at least 40 mg, or even 50 mg, 75 mg, 100 mg, 150 mg or 250 mg of biotin per unit dose.

This injectable composition may be in the form of a vial containing the biotin, and also acceptable excipients. The concentration of biotin is adjusted according to the envisaged volume of the vial. Certain excipients which improve biotin solubility can be used.

The excipients that can be used for the production of injectable compositions are well known in the art. Mention may in particular be made of sodium dihydrogen phosphate, sodium bicarbonate (E550i), methyl para-hydroxybenzoate (E218) and propyl para-hydroxybenzoate (E216), which can be used together in proportions that those skilled in the art are capable of determining. The water used is water for injection. The injection is preferably carried out intramuscularly. It can also be carried out intravenously.

EXAMPLES

One patient suffering from AMN was treated for 5 month with high doses of biotin (100 to 300 mg/day) and showed marked clinical improvement after a delay of 3 months (see below). Treatment was then arrested for 1½ month resulting in worsening with return to baseline. After reintroduction, the patient improved again. This case report is detailed below. The fact that this patient responded to biotin suggests that high doses of biotin are efficacious in modifying evolution of AMN and/or alleviating the symptoms of the disease. These results shall later be confirmed in a placebo randomized clinical trial.

Clinical Case

This 44 year-old patient born in 1969 was diagnosed with adrenomyeloneuropathy in 2012. The diagnosis was confirmed genetically with a pathogenic mutation (c.584A>G) in the ABCD1 gene. He had a 15 years history of progressive spastic paraparesis with urinary problems (urinary urgencies). Treatment with biotin was started in early February 2013 at 100 mg/day. At that time, the patient was able to walk independently with no limitation of his walking distance. However, he exhibited marked spasticity in lower limbs together with urinary problems: he had to wake up several times during the night because of urinary urgencies. He used a urethral catheter before sleep and once at night to empty his bladder. The best time to walk 15 meters (corridor length) was 17 seconds. Treatment with biotin was started for three months. After this period, no significant change was noticed: the best time to walk 15 meters was 15 seconds with an improvement of 11.7% compared to baseline which was considered as non significant. No change in urinary problems was noticed. During this period, the patient was followed by a physical therapist two times a week with no noticeable improvement at different tests (Table 1).

TABLE 1

Follow-up with physical therapy two times a week.

| Week | Exercice 1 Knees up on trampoline (1 min) | Exercice 2 Leg scissors on trampoline | Exercice 3 Leg scissors on trampoline with elastic resistance | Exercice 4 Leg scissors on the floor |
|---|---|---|---|---|
| 1 | 78 | 43 | 24 in 30" | 20 |
|   | 78 | 51 in 58" | 28 in 30" | 28 in 27" |
| 2 | 83 | 50 in 53" | 30 in 31" | 16 in 15" |
|   | 93 | 62 in 1'05" | 40 in 45" | 20 in 19" |
| 3 | 98 | 66 in 1'07" | 60 in 1'05" | 22 in 21" |
|   | 92 | 60 in 1'03" | 52 in 56" | 26 in 26" |

TABLE 1-continued

Follow-up with physical therapy two times a week.

| Week | Exercice 1 Knees up on trampoline (1 min) | Exercice 2 Leg scissors on trampoline | Exercice 3 Leg scissors on trampoline with elastic resistance | Exercice 4 Leg scissors on the floor |
|---|---|---|---|---|
| 4 | 99 | 70 in 1'17" | 41 in 43" | 22 in 22" |
|  | 95 | 80 in 1'27 | 60 in 1'05" | 30 in 29" |
| 5 | NA | NA | NA | NA |
|  | 99 | 62 in 1'08" | 49 in 57" | 20 in 19" |
| 6 | 100 | 76 in 1'22" | 68 in 1'13" | 24 in 23" |
|  | NA | NA | NA | NA |
| 7 | 101 | 82 in 1'28" | 90 in 1'40 | 35 in 33" |
|  | 101 | 97 in 1'40" | 93 in 1'42 | 33 in 33" |
| 8 | NA | NA | NA | NA |
|  | NA | NA | NA | NA |
| 9 | NA | NA | NA | NA |
|  | NA | NA | NA | NA |
| 10 | 90 | 62 in 1'09" | 70 in 1'16 | 22 in 22" |
|  | 100 | 69 in 1'18" | 54 in 1'01" | 34 in 33" |
| 11 | 97 | 67 in 1'13" | 88 in 1'38" | 19 in 18" |
|  | 97 | 71 in 1'20" | 55 in 1'01" | 31 in 32" |
| 12 | 97 | 72 in 1'23" | 48 in 56" | 38 in 37" |
|  | 103 | 63 in 1'12" | 88 in 1'38" | 39 in 39" |
| Mean +/− SD | 94.5 +/− 7.6 | 66.8 +/− 12.6 | 57.7 +/− 21.7 | 26.6 +/− 7 |

NA: non available.
Column 1: weeks of examinations, column 2: maximum number of «knees up» on a trampoline in less than 1 minute, column 3: maximum number of leg scissor movements on a trampoline, column 4: same as column 3 but with an elastic around his legs, column 5: same as column 3 but on the floor. Between early February (treatment start), and end of April (3 months of treatment), numbers were comparable.

After 3 months (May 2013), the dosage was increased to 300 mg/day. One month later (June 2013) the patient noticed improvement of spasticity and urinary problems. The best time to walk 15 meters was 14.3 seconds (−15.9% compared to the pre-treatment value which can be considered as clinically meaningful). In the mean while, the patient noticed marked improvement of urinary problems. Urinary urgencies had markedly decreased during the night and the patient was not obliged to use a urethral catheter during the night. The dosage (300 mg/day) was pursued for one month more. At Month 5 (July 2013), the best time to walk 15 meters was 13.7 seconds (−19.4% compared to the pre-treatment value). Urinary urgencies remained improved to the same level than at 4 months. Physical therapy follow-up between the first of May and end of June 2013 (M4 to M5) showed a marked improvement of all parameters including maximum number of knees up on a trampoline in less than 1 minute (+31.9%), maximum number of leg scissor movements on a trampoline (+67.7%), maximum number of leg scissor movements on a trampoline with elastic resistance (+103%), maximum number of leg scissor movements on the floor (+43.2%, tables 2 and 3).

TABLE 2

Physical therapy follow-up two times a week during the M4 to M5 period.

| Week | Exercice 1 Knees up on trampoline (1 min) | Exercice 2 Leg scissors on trampoline | Exercice 3 Leg scissors on trampoline with elastic resistance | Exercice 4 Leg scissors on the floor |
|---|---|---|---|---|
| 13 | 108 | 80 in 1'30 | 109 in 2'03 | 30 in 31" |
| 14 | 106 | 104 in 1'53 | 125 in 2'16" | 35 in 35" |
|  | 133 | 120 in 2'12 | 100 in 1'54" | 40 in 41" |
| 15 | NA | NA | NA | NA |
|  | NA | NA | NA | NA |
| 16 | NA | NA | NA | NA |
|  | 126 | 73 in 1'22" | 57 in 1'05" | 35 in 36" |
| 17 | 120 | 130 in 2'19 | 129 in 1'14" | 46 in 46" |
|  | 133 | 148 in 2'40" | 152 in 2'42" | 48 in 48" |
| 18 | 127 | 84 in 1'30" | 88 in 1'38" | 41 in 41" |
|  | NA | NA | NA | NA |
| 19 | 131 | 140 in 2'34" | 134 in 2'37" | 39 in 38" |
|  | NA | NA | NA | NA |
| 20 | 130 | 110 in 2'00" | 133 in 2'26" | 31 in 31" |
|  | 1. |  |  |  |
| 21 | 133 | 132 in 2'24" | 147 in 2'36" | 36 in 25" |
| Mean +/− SD | 124.7 +/− 10.2 | 112 +/− 26.4 | 117.4 +/− 29.2 | 38.1 +/− 5.9 |

NA: not available.
Column 1: dates of examinations, column 2: maximum number of knees up on a trampoline in less than 1 minute, column 3: maximum number of leg scissor movements on a trampoline, column 4: same as column 3 but with an elastic around his legs, column 5: same as column 3 but on the floor. Compared with table 1 all numbers in creased (see TABLE 3).

TABLE 3 comparisons of different physical therapy exercises between the M0-M3 period (week 0 to week 12) and the M4-M5 period (week 13 to week 21).

| Type of exercise | Mean +/− SD Week 0 to Week 12 | Mean +/− SD Week 13 to Week 21 | % improvement | P value* |
|---|---|---|---|---|
| Knees up on trampoline (1 min) | 94.5 +/− 7.6 | 124.7 +/− 10.2 | +31.9 | <0.0001 |
| Leg scissors on trampoline | 66.8 +/− 12.6 | 112 +/− 26.4 | +67.7 | 0.0003 |
| Leg scissors on trampoline with elastic resistance | 57.7 +/− 21.7 | 117.4 +/− 29.2 | +103 | <0.0001 |
| Leg scissors on the floor | 26.6 +/− 7 | 38.1 +/− 5.9 | +43.2 | 0.00012 |

*bilateral student's t test for unpaired data comparing M0-M3 values to M4-M5 values.

At Month 5, a brain MRI with brain NMR spectroscopy (NMRS) was performed in the brain white matter. This showed some improvement of the N-acetyl aspartate (NAA)/creatine (Cr) ratio compared to baseline (table 4).

TABLE 4

Changes in NMR spectroscopy parameters between 2013 Jan. 26 (before treatment) and 2013 Jun. 25 (after treatment). Note an increase in the NAA/Cr ratio from 1.67 to 1.81.

|  | M0: 2013 Jan. 26 | M5: 2013 Jun. 25 |
|---|---|---|
| NAA | 20.00 | 29.00 |
| Cr | 12.00 | 16.00 |
| Ch | 18.00 | 25.00 |
| NAA/Cr | 1.67 | 1.81 |
| Ch/Cr | 1.50 | 1.56 |
| Ch/NAA | 0.90 | 0.86 |

Treatment with biotin was then stopped in July 2013 (at M5). After 10 days of treatment arrest, the patient noticed some worsening of walking and of urinary problems. When he was seen at the end of August 2013 (after 1½ month of treatment arrest), the best time to walk 15 meters had returned to 17.2 seconds (+1.2% compared to baseline value). The patient was using a urethral catheter again during the night.

Treatment was then reintroduced at 300 mg/day. After a week, the patient noticed some improvement of urinary urgencies. When he was seen one month after reintroduction of the treatment, the best time to walk 15 meters was 14.6 seconds (−14.1% compared to baseline).

TABLE 5

Evolution of the best time to walk 15 meters at different time points (see text)

| Patient | Best time (one go) | % change from baseline |
|---|---|---|
| M0 (before treatment) | 17 sec | |
| M3 (after 3 months) | 15 sec | −11.7% |
| M4 | 14.3 sec | −15.9% |
| M5 | 13.7 sec | −19.4% |
| 1.5 month after arrest | 17.2 sec | +1.2% |
| 1 month after reintroduction | 14.6 sec | −14.1% |

Discussion

Overall, this observation indicates a benefit of treatment with high doses of biotin in patients with AMN. The demonstration of treatment's efficacy relies on several observations in the same patient.
1) Clinical tests including the best time to walk 15 meters as well as physical therapy measures clearly showed an improvement while on treatment.
2) Improvement of clinical symptoms such as urinary urgencies and ability to avoid urethral catheter at night are reminiscent of drug's efficacy.
3) Improvement of the NAA/Cr ratio is usually considered as a robust marker of neuronal health. An increase in this ratio after treatment suggests some neuronal recovery after 5 months of treatment.
4) Worsening of the clinical status after drug withdrawal and re-improvement after drug re-introduction strongly suggests that improvement has been caused by the drug and is not linked to spontaneous evolution or to physical therapy training.
5) The fact that the patient improved after increasing the dosage from 100 to 300 mg strongly suggests a dose-effect.
6) The fact that the patient improved after at least 3 months of treatment and that improvement was sustained during months 4 and 5 is against a placebo effect which usually appears shortly after drug introduction.

These results thus support treatment efficacy of high doses of biotin in AMN, and shall be confirmed in a placebo-controlled-double blind-randomized clinical trial.

REFERENCES

Fourcade S et al, Early oxidative damage underlying neurodegeneration in X-adrenoleukodystrophy. Hum Mol Genet. 2008 Jun. 15; 17(12):1762-73. Epub 2008 Mar. 14

Powers J M et al, Adreno-leukodystrophy: oxidative stress of mice and men. J Neuropathol Exp Neurol. 2005 Dec.; 64(12):1067-79.

The invention claimed is:

1. A method for treating adrenomyeloneuropathy, comprising administering to a patient in need thereof a composition comprising biotin and a pharmaceutically acceptable excipient, wherein the daily amount of biotin administered to the patient is at least 250 mg.

2. The method according to claim 1, wherein the daily amount of biotin administered to the patient is at least 300 mg.

3. The method according to claim 1, wherein the composition is in a form suitable for oral administration.

4. The method according to claim 1, wherein the composition is in the form of gel capsules, tablets, lozenges or pills.

5. The method according to claim 1, wherein biotin is the sole active ingredient.

6. The method according to claim 1, wherein the excipient is chosen from the group consisting of talc, microcrystalline cellulose, lactose and mannose.

7. The method according to claim 1, wherein the composition is in a form suitable for injectable administration.

8. The method according to claim 1, wherein the composition is in the form of a slow release composition.

9. The method according to claim 1, wherein the composition further comprises another drug against adrenomyeloneuropathy for simultaneous, separate or sequential use in the treatment of adrenomyeloneuropathy.

10. The method according to claim 9, wherein said other drug is Lorenzo's oil or Fampridine.

11. The method according to claim 4, wherein the tablets are film-coated.

12. The method according to claim 9, wherein the sequential use is spread out over time.

13. The method according to claim 1, wherein the daily amount of biotin administered to the patient is about 300 mg.

* * * * *